United States Patent
Pfister

(10) Patent No.: US 8,588,489 B2
(45) Date of Patent: Nov. 19, 2013

(54) METHOD FOR DISPLAYING A VESSEL OF A PARTICULAR BIOLOGICAL SUBJECT

(75) Inventor: Marcus Pfister, Bubenreuth (DE)

(73) Assignee: Siemens Aktiengesellschaft, München (DE)

(*) Notice: Subject to any disclaimer, the term of this patent is extended or adjusted under 35 U.S.C. 154(b) by 263 days.

(21) Appl. No.: 13/228,712

(22) Filed: Sep. 9, 2011

(65) Prior Publication Data

US 2012/0082363 A1  Apr. 5, 2012

(30) Foreign Application Priority Data

Sep. 30, 2010 (DE) .......................... 10 2010 041 735

(51) Int. Cl.
*G06K 9/00* (2006.01)
*G06K 9/32* (2006.01)

(52) U.S. Cl.
USPC .......................... 382/128; 362/132; 362/300

(58) Field of Classification Search
USPC ................... 382/128, 132, 300, 133
See application file for complete search history.

(56) References Cited

U.S. PATENT DOCUMENTS

| | | | |
|---|---|---|---|
| 6,996,260 B1* | 2/2006 | Skands et al. ................. | 382/128 |
| 7,383,164 B2* | 6/2008 | Aram et al. ...................... | 703/7 |
| 7,959,572 B2* | 6/2011 | Ishihara ........................ | 600/437 |
| 8,374,401 B2* | 2/2013 | Sugimura et al. ............. | 382/115 |
| 8,423,121 B2* | 4/2013 | Wang et al. .................... | 600/424 |
| 2009/0105579 A1* | 4/2009 | Garibaldi ...................... | 600/409 |
| 2010/0061611 A1* | 3/2010 | Xu et al. ........................ | 382/131 |
| 2010/0198330 A1 | 8/2010 | Hossainy et al. | |
| 2010/0215149 A1 | 8/2010 | Ohishi | |
| 2011/0103666 A1* | 5/2011 | Ohishi .......................... | 382/131 |

FOREIGN PATENT DOCUMENTS

DE  10 2010 012 621.7  3/2010

OTHER PUBLICATIONS

Graeme P. Penney and Philipp G. Batchelor and Derek L. G. Hill and David J. Hawkes and Juergen Weese, "Validation of a two- to three-dimensional registration algorithm for aligning preoperative CT images and intraoperative fluoroscopy images," 2001, Medical Physics, vol. 28.*

* cited by examiner

*Primary Examiner* — Utpal Shah

(57) ABSTRACT

A method for displaying a vessel of a particular biological subject is proposed. The particular object is inserted into the vessel. The deformation of the vessel is predicted by an inserted object on the basis of experience. This experience is quantified by assigning values to particular parameters, the parameters providing information concerning characteristics of the patient, characteristics of his/her vessel and information about the interventional instrument inserted.

16 Claims, 2 Drawing Sheets

METHOD FOR DISPLAYING A VESSEL OF A PARTICULAR BIOLOGICAL SUBJECT

CROSS REFERENCE TO RELATED APPLICATIONS

This application claims priority of German application No. 10 2010 041 735.1 filed Sep. 30, 2010, which is incorporated by reference herein in its entirety.

FIELD OF THE INVENTION

The invention relates to a method for displaying a vessel of a particular biological subject, wherein a particular object is inserted into said vessel.

BACKGROUND OF THE INVENTION

The invention is linked to the method for automatically adapting a reference image which is proposed in DE 10 2010 012 621.7 published after the filing date of the present application.

The particular objective here is to display an aorta of a human patient. This is advantageous in connection with the treatment of an abdominal aortic aneurysm. An abdominal aortic aneurysm is an "outpouching" on the abdominal aorta. To repair it, a so-called stent is inserted, i.e. an angioplasty. To insert such a stent, care must be taken to ensure correct placement. In order to facilitate same for the treating physician, fluoroscopic images (X-ray pictures) of the patient can be taken continuously during stent positioning. In order to avoid having to inject new contrast agent continuously into the patient, low-contrast fluoroscopic images can be taken and overlaid with a reference image which enables sufficient orientation. The reference image can be a 2D angiogram. It is advisable if, prior to treatment, a 3D image data set in respect of the aneurysm is acquired, e.g. using computed tomography angiography. Such reference data sets are sometimes pre-segmented, i.e. undergo an image processing step in which particular structures are particularly accentuated in the image. At its simplest, segmentation takes the form of extreme contrast intensification. For example, segmentation can be used to accentuate the walls of the aorta in black, while the interior of the aorta appears white.

The overlaying of the reference image with the currently captured fluoroscopic image is then performed by per se known methods for merging two images into one. For this purpose, in particular the reference systems in which the individual images were captured must be set in relation to one another by calculating a mapping rule (so-called "registration").

To introduce a stent, guide wires and catheters are inserted into the aorta. Inserting such objects into the aorta may cause deformation of the vessel walls, particularly if the objects and instruments are very rigid. In DE 10 2010 012 621.7 it is now described that, in the event of particularly severe deformation during which the currently taken fluoroscopic images show something different from the existing reference images, these reference images themselves undergo further processing, namely to calculate how the inserted object deforms the vessel walls.

In DE 10 2010 012 621.7, deformation predictability is assumed. This predictability actually exists in the case of recurring conditions.

However, the actual conditions may be subject to significant variation: for example, in one instance a short, slightly-built male patient may be involved, another time a tall, stoutly-built female patient. Also the instruments used may be different from one another. It would therefore be desirable for the method for displaying a vessel to be able to take this variability into account in some way.

SUMMARY OF THE INVENTION

The object of the present invention is therefore to demonstrate how a method for displaying a vessel, in which the vessel walls shown in a reference image are modified by calculation, can be made applicable over a wide spectrum while still operating in a precise manner.

This object is achieved by a method having the features set forth in the claims.

The method according to the invention begins with first individually characterizing a plurality of biological subjects similar to the particular biological subject by assigning values to first predefined parameters in each case. It is therefore attempted, by defining said first predefined parameters, to make the biological subjects "measurable" in some way. The parameters need not be numerically ascertainable measured variables; rather the parameters can also be specifiable by a binary number (e.g. in respect of the sex of the biological subject); in the same way, many parameters can also be assigned three or more values corresponding to particular characteristics of the biological subject or classes of characteristics (e.g. "non-smoker"; "occasional smoker"; "heavy smoker").

In the same way as a plurality of similar biological subjects are characterized, a plurality of objects similar to the particular object inserted into the biological subject are now also characterized in step b); the similarity is specifically reflected in the fact that these objects are all insertable into the same vessel in different biological subjects. Said plurality of insertable objects are individually characterized by assigning values to two predefined parameters.

In the subsequent step, for at least some of the plurality of subjects and/or at least some of the plurality of objects, step c) is carried out whereby measured values are obtained, namely as values of deformation parameters describing a deformation of the relevant vessel when one of the plurality of objects is being inserted into one of the plurality of subjects. These measured values can be obtained automatically or acquired independently of the work of the physician by a measurement physicist. The measured values shall in particular be ones which, when known, subsequently enable changes to be made in the display.

Alternatively to carrying out steps a), b), c), the method according to the invention can also be seen implemented if a data set is already available which is accessed or is made available as the case may be. In this case the data set contains vectors which comprise the values for the first predefined parameters, the values for the second predefined parameters and the measured values for a plurality of combinations of biological subjects and objects.

In both variants, the method according to the invention continues as follows: in respect of the particular subject, it is characterized in step d) by assigning values to the first predefined parameters, and the particular object inserted is also characterized likewise in step e) by assigning values to the second predefined parameters. In step g), on the basis of the first and second parameter values which were assigned in step d) and e) and of at least some of the measured values which were obtained in step c) or are available in the data set in corresponding vectors, together with the assigned first and second parameters, deformation parameter values are then inferred which describe the deformation of the particular vessel by the particular object.

A kind of "experience" is therefore built up which is acquired for different biological subjects (patients) by inserting different kinds of inserted objects (instruments), and the deformation parameter values are inferred on the basis of this experience. This is preferably carried out automatically by a computer system according to a predefined algorithm. However, the deformation parameters can also be determined in other ways, in particular with human involvement.

In step f) before or after step g), a fluoroscopic image (X-ray image) of the vessel of the particular biological subject without inserted object is obtained. Step f) is usually carried out prior to insertion of the object, or when the object is not yet completely inserted, so that no, or no appreciable, deformation of the vessel walls has taken place. In step h) a modified fluoroscopic image is now calculated on the basis of the fluoroscopic image acquired in step f) and the deformation parameters obtained in step g).

The present invention goes beyond the method described in DE 10 2010 012 621.7 in that it demonstrates a way in which the deformation parameters, which were hitherto assumed to be readily ascertainable, can also be determined under circumstances of great complexity resulting from the multiplicity of lifestyle circumstances.

In the preferred embodiment of the invention, the biological subject is, as already described in the introduction, a human patient. The first predefined parameters then preferably comprise parameters pertaining to the patient as a whole which relate in particular to the patient's age, height, sex, weight as well as information concerning his/her medical history, and also to whether he/she is a smoker, a diabetic, or shows any genetic abnormalities, etc. Equally, the first predefined parameters can also comprise parameters pertaining to the vessel and its contents, which relate e.g. to calcium levels, to locations where calcification is present, to the thickness of a blood clot (thrombus), to the thickness of a vessel (lumen), etc.

In a preferred embodiment, the particular object is also, as likewise mentioned in the introduction, a medical instrument, namely in particular an invasive device, and the second predefined parameters then preferably relate to its size and/or rigidity.

With the method according to the invention the currently acquired fluoroscopic image of the particular object inserted into the vessel is preferably also overlaid with the modified fluoroscopic image calculated in step h) (the overlaying is merged rendering of the two images).

The fluoroscopic image obtained in step f) preferably undergoes a step of accentuating predetermined structures, particularly the vessel walls (see the above explanations concerning "segmentation").

There are various possibilities for obtaining the measured values in step c), or more specifically the deformation parameters for the data set. In one alternative, the measured values are acquired by at least one position sensor on the inserted object. Alternatively they can be obtained from fluoroscopic images, i.e. automatically, or such fluoroscopic images can be shown to a treating person and the image data processing system then receives a manual input from said person after the fluoroscopic image is displayed.

In all these embodiments, the measured values are preferably coordinates of particular locations on the vessel walls. If said measured values specify deformation parameters for those parameter combinations of the first and second parameters for which there are no measured values, these deformation parameters are also to be regarded as coordinates, and interpolation between these coordinates takes place in step h).

Various possibilities are conceivable for the inferring in step g). The inferences are preferably made automatically in step g) using a neural network (that is artificial, i.e. one which is generated virtually in a data processing device). It is likewise also conceivable to use a conventional algorithm, e.g. in the form of a formula which contains the variables and whose value must be minimized. In this case a gradient descent method can be used, for example.

BRIEF DESCRIPTION OF THE DRAWINGS

A preferred embodiment of the invention will now be described with reference to the accompanying drawings in which.

DETAILED DESCRIPTION OF THE INVENTION

To treat an abdominal aortic aneurysm, a stent is to be inserted into the aorta. In preparation for the insertion of the stent, a catheter is inserted into the aorta. The insertion of the stent is to be assisted by imaging. For this purpose, prior to the interventional procedure a reference image of the patient is taken. During the interventional procedure additional fluoroscopic images are acquired at low X-ray dose. The fluoroscopic images are superimposed on the reference image. However, as the insertion of the catheter causes deformation of the vessel walls of the aorta, the fluoroscopic image and the reference image per se would no longer match up directly. The aim is now to rectify this by modifying the reference image: if the behavior of the catheter in the aorta is known, the deformation can be predicted.

However, the behavior of the aorta during insertion of the catheter is only known on the basis of past experience. This is acquired primarily by inserting a more or less identical invasive instrument into a plurality of patients into the same aorta in each case, both the patient, his/her aorta and the invasive instrument being characterized by assigning values to particular parameters. The deformation is then measured and corresponding deformation parameters are assigned to the other parameters. If this is done for the plurality of patients and interventional instruments, a data set is available which more or less reflects "experience".

In detail, the procedure is as follows:

Let $X1(j)$ with $j=1, \ldots K$ be parameters describing the patient, e.g. his/her age, sex, height, whether he/she is a smoker or diabetic, whether he/she has genetic abnormalities, and they can reflect the patient's medical history. Let $X2(k)$ with $k=1, \ldots L$ be physiological parameters of the aorta, e.g. the so-called "calcium score", specifying the locations of calcifications, the local diameter of the vessel (lumen diameter), the local thickness of a blood clot (thrombus), etc.

Finally, the parameters $X3(l)$ with $l=1, \ldots M$ specify properties of the inserted instrument, e.g. its size and rigidity.

Some of the parameters can be specified like a numerical value, e.g. by a natural number or a real number. Another portion of the parameters can be specified by logical values, i.e. can be binary, for example, as this suffices for specifying whether or not the patient is diabetic.

Figure 1:
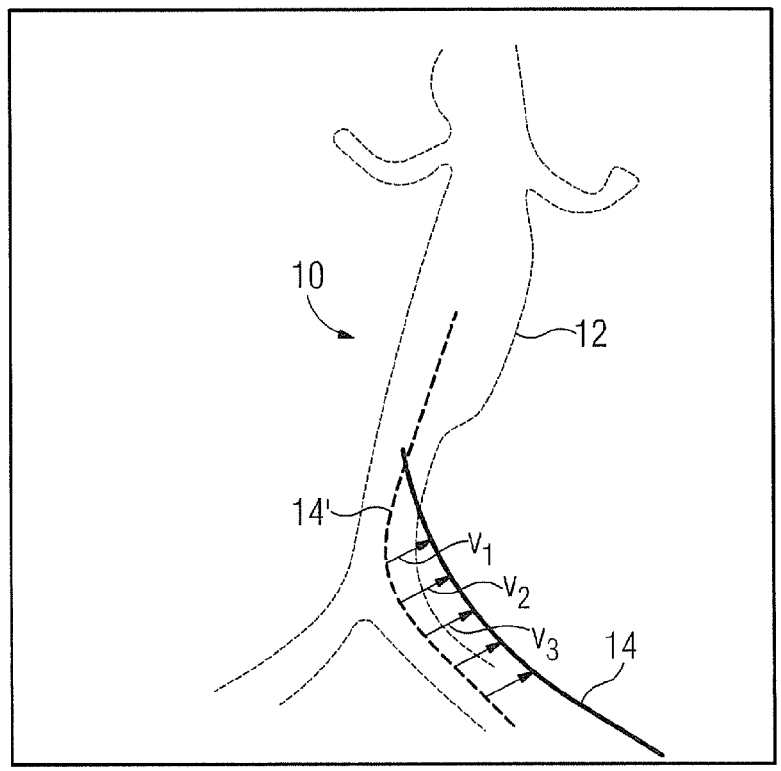
FIG. 1, FIG. 2 schematically illustrate an aorta into which a surgical instrument is inserted, these Figures serving to explain how an image of the vessel walls of the aorta can be corrected.
Figure 2:
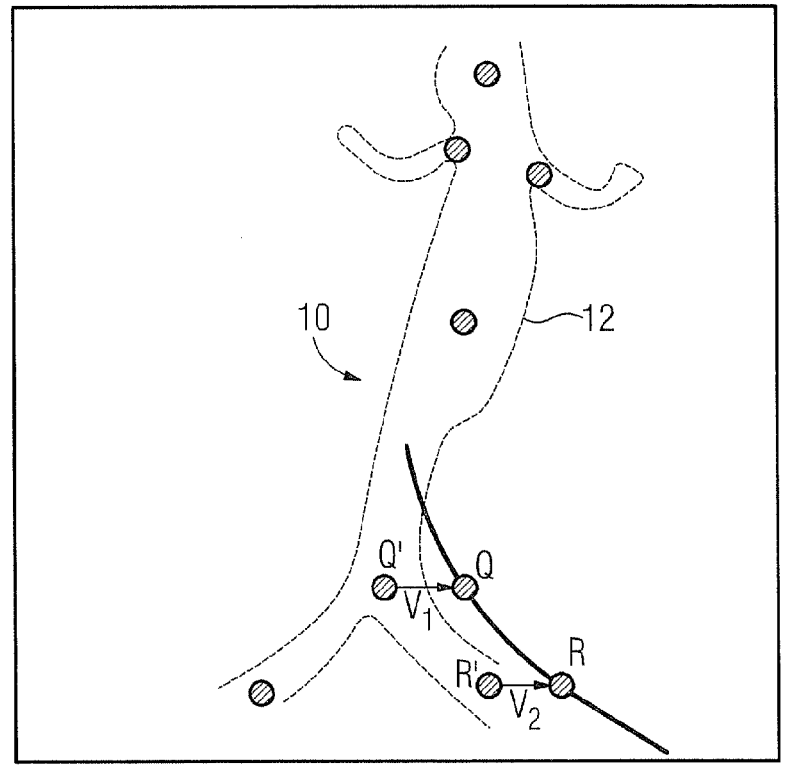
Figure 3:
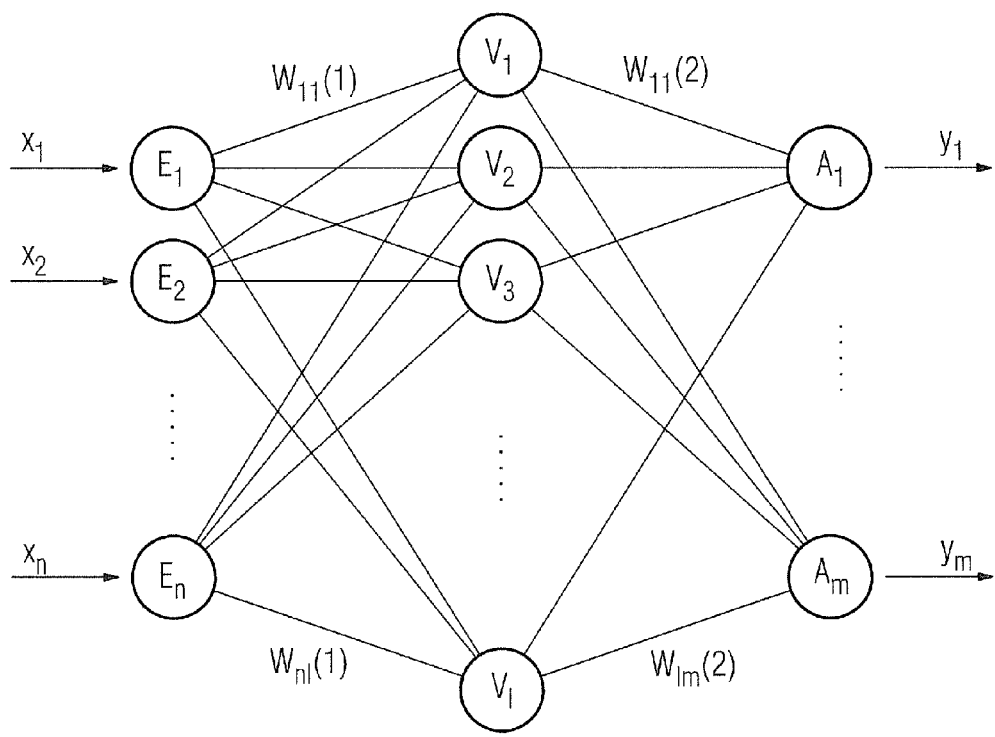
FIG. 3 shows a block schematic of a neural network.

Deformation parameters shall now be measured. FIG. 1 shows an aorta 10 with an aneurysm 12. A catheter 14 is to be inserted into the aorta. The dashed outline of the aorta 10 corresponds to the outline prior to the insertion of the catheter. This is mapped e.g. in a reference image which has undergone a segmentation step. The catheter 14 can be seen in fluoroscopic images taken during the intervention. If the reference image and fluoroscopic image are superimposed, it may be that the catheter 14 is seen outside the aorta 10. It is therefore necessary to adapt the outline of the aorta 10. FIG. 1 shows schematically by means of the dashed line 14' which path the catheter 14 would take in the aorta if the latter were not to deform. The vectors $v_1$, $v_2$, $v_3$, etc. indicate the extent to which the aorta 10 has obviously deformed. Although the vectors $v_1$, $v_2$, $v_3$, etc. can be assigned to the entire surface of the catheter 14, individual points Q, R can also be selected as shown in FIG. 2, and a displacement vector $V_1$, $V_2$ can be derived on the basis of these points.

The vectors $v_i$ or $V_i$ can be derived from fluoroscopic images, or alternatively can be acquired using a position sensor.

It is therefore clear that some parameters can be measured which specify the displacement. These shall be combined into a vector $\Delta P$. The other parameters shall be combined into the vectors $\overline{X1}$, $\overline{X2}$, $\overline{X3}$.

It shall now be assumed that there is a function F which can calculate the deformation vector $\Delta P$ from the input vectors $\overline{X1}$, $\overline{X2}$, $\overline{X3}$ only using calculation parameters W(p), p=$\overline{1, \ldots R}$. A function $F(\overline{X1}, \overline{X2}, \overline{X3}, \overline{W}) = \overline{\Delta P}$ is therefore sought.

On the basis of the measured values which are obtained using a plurality of patients and interventional instruments, the function can be gradually determined and the defoiniation parameters can then be calculated subsequently for subjects on which the deformation measurement is not performed. The reference image can therefore be adapted when measured values are not available because an interventional procedure is being carried out on a patient.

The function can be any kind of parameterizable function, ranging from simple linear functions, to polynomials, to complex nonlinear functions. Specifying a precise function may require a high degree of computational complexity. Therefore the use of fuzzy logic can also be recommended. The function F can likewise also be gradually learnt by a neural network which can also be provided by an algorithm as an artificial neural network.

Recourse may be made to the following algorithm: for a set of input and output values $L_iX$ and $L_i\Delta P$ for i=1, ... Q combination[s] of patients and interventional instruments, the vector $\underline{W}$ fulfilling the following function is sought $$\sum_{i=1}^{Q} \left\| \frac{dF(L_iX_1, L_iX_2, L_iX_3, W)}{dW} L_i\Delta P \right\| = \min.$$

The solution can be iteratively approximated by an algorithm, e.g. using the so-called gradient descent method, namely until a local minimum has been found for which $$\frac{dF(X1, X2, X3, W)}{dW} = 0.$$

As an alternative to this approach, a neural network can be used. There are input values $x_i$ which are entered in an input layer with elements $E_i$, and after processing in a hidden layer with element $V_i$ there is produced an output of output values $y_i$ by output elements $A_i$. If the $y_i$ denote the segmentation parameters (e.g. of the centerline splines), these can be calculated in the case of known calculation parameters ($W_{ij}$) by the corresponding input values. The calculation parameters are determined by the neural network as part of a learning process. Neural networks can "learn" particular values based on experience.

On the basis of the empirical values, it can therefore be regularly deduced in the case of new patients how a particular vessel will deform the aorta 10. However, this enables a reference image to be adapted in the manner of the method described in DE 10 2010 012 621.7 published after the filing date of the present application, after current fluoroscopic images are overlaid. What is seen on the fluoroscopic image will then coincide with what is seen on the reference image.

The invention claimed is:

1. A method for displaying a vessel of a particular biological subject into which a particular object is inserted, comprising:

individually assigning a first predefined parameter to a plurality of the biological subjects similar to the particular biological subject;

individually assigning a second predefined parameter to a plurality of objects that can be inserted into a respective same type of the vessel in the plurality of biological subjects;

obtaining a measured deformation parameter value describing a deformation of the respective same type of the vessel when one of the plurality of objects is inserted into one of the plurality of the biological subjects;

assigning the first predefined parameter to the particular subject;

assigning the second predefined parameter to the particular object;

acquiring a fluoroscopic image of the vessel of the particular biological subject without the particular object inserted;

inferring a deformation parameter value describing a deformation of the vessel when the particular object is inserted into the particular subject based on the assigned first and second parameter values and the measured deformation parameter value; and calculating a changed fluoroscopic image of the vessel based on the acquired fluoroscopic image and the inferred deformation parameter value.

2. The method as claimed in claim 1, wherein the particular biological subject is a patient.

3. The method as claimed in claim 2, wherein the first predefined parameter is selected from the group consisting of: age of the patient, height of the patient, sex of the patient, weight of the patient, and medical history information of the patient.

4. The method as claimed in claim 3, wherein the medical history information of the patient comprises whether the patient is a smoker, whether the patient is diabetic, whether the patient shows genetic abnormalities, and a parameter of the vessel.

5. The method as claimed in claim 4, wherein the parameter of the vessel comprises a calcium count of the vessel, location of the calcification, thickness of a blood clot, and thickness of the vessel.

6. The method as claimed in claim 1, wherein the particular object is an invasive device.

7. The method as claimed in claim 6, wherein the second predefined parameter comprises size and/or rigidity of the invasive device.

8. The method as claimed in claim 1, further comprising acquiring a current fluoroscopic image of the vessel with the particular object inserted and overlaying the current acquired fluoroscopic image with the changed fluoroscopic image.

9. The method as claimed in claim 1, further comprising accentuating a predetermined structure of the vessel of the fluoroscopic image without the particular object inserted.

10. The method as claimed in claim 9, wherein the predetermined structure of the vessel comprises a vessel wall.

11. The method as claimed in claim 1, wherein the measured deformation parameter value is obtained by a position sensor arranged on the particular object inserted.

12. The method as claimed in claim 1, wherein the measured deformation parameter value is obtained automatically based on a fluoroscopic image of the respective same type of the vessel when one of the plurality of objects is inserted into one of the plurality of the biological subjects.

13. The method as claimed in claim 1, wherein the measured deformation parameter value is obtained by receiving a manual input after displaying a fluoroscopic image of the respective same type of the vessel when one of the plurality of objects is inserted into one of the plurality of the biological subjects.

14. The method as claimed in claim 1, wherein the measured deformation parameter value is coordinates of a location on a wall of the vessel and the deformation parameter value is coordinates interpolated based on the measured deformation parameter value.

15. The method as claimed in claim 1, wherein the deformation parameter value is inferred using an artificial neural network and/or an algorithm.

16. The method as claimed in claim 15, wherein the algorithm comprises a gradient descent method.

* * * * *